United States Patent [19]

Mitchell

[11] 4,125,905
[45] Nov. 21, 1978

[54] WASHING ATTACHMENT FOR ARTIFICIAL ARMS

[76] Inventor: Joseph I. Mitchell, 8259 S. Peoria, Chicago, Ill. 60620

[21] Appl. No.: 763,403

[22] Filed: Jan. 28, 1977

[51] Int. Cl.² .............................................. A61F 1/06
[52] U.S. Cl. ...................................................... 3/12.8
[58] Field of Search ................ 3/12.8, 12, 12.4, 12.5, 3/12.1, 12.2, 12.3; 15/244 R, 244 A, 244 B, 244 C; 401/23, 203, 204

[56] References Cited

U.S. PATENT DOCUMENTS

| 483,090 | 9/1892 | Wortham | 3/12.1 |
|---|---|---|---|
| 1,625,317 | 4/1927 | Hodgson | 3/12 |
| 2,501,289 | 3/1950 | Orndorff | 401/204 |
| 3,490,078 | 1/1970 | Perez | 3/12.8 |
| 3,526,918 | 9/1970 | Leland | 15/244 R X |

OTHER PUBLICATIONS

"Orthopaedic Appliances Atlas" vol. 2 (Artificial Limbs) J. W. Edwards, Ann Arbor, Michigan, 1960, pp. 95–97.

*Primary Examiner*—Ronald L. Frinks
*Attorney, Agent, or Firm*—W. Melville Van Sciver

[57] ABSTRACT

An attachment for artificial arms, particularly for multiple arm amputees, to enable the amputee to wash all parts of his or her body. The washing elements are secured to artificial arms which are adapted to be secured to the live portion of each arm of the amputee.

2 Claims, 4 Drawing Figures

U.S. Patent
Nov. 21, 1978
4,125,905
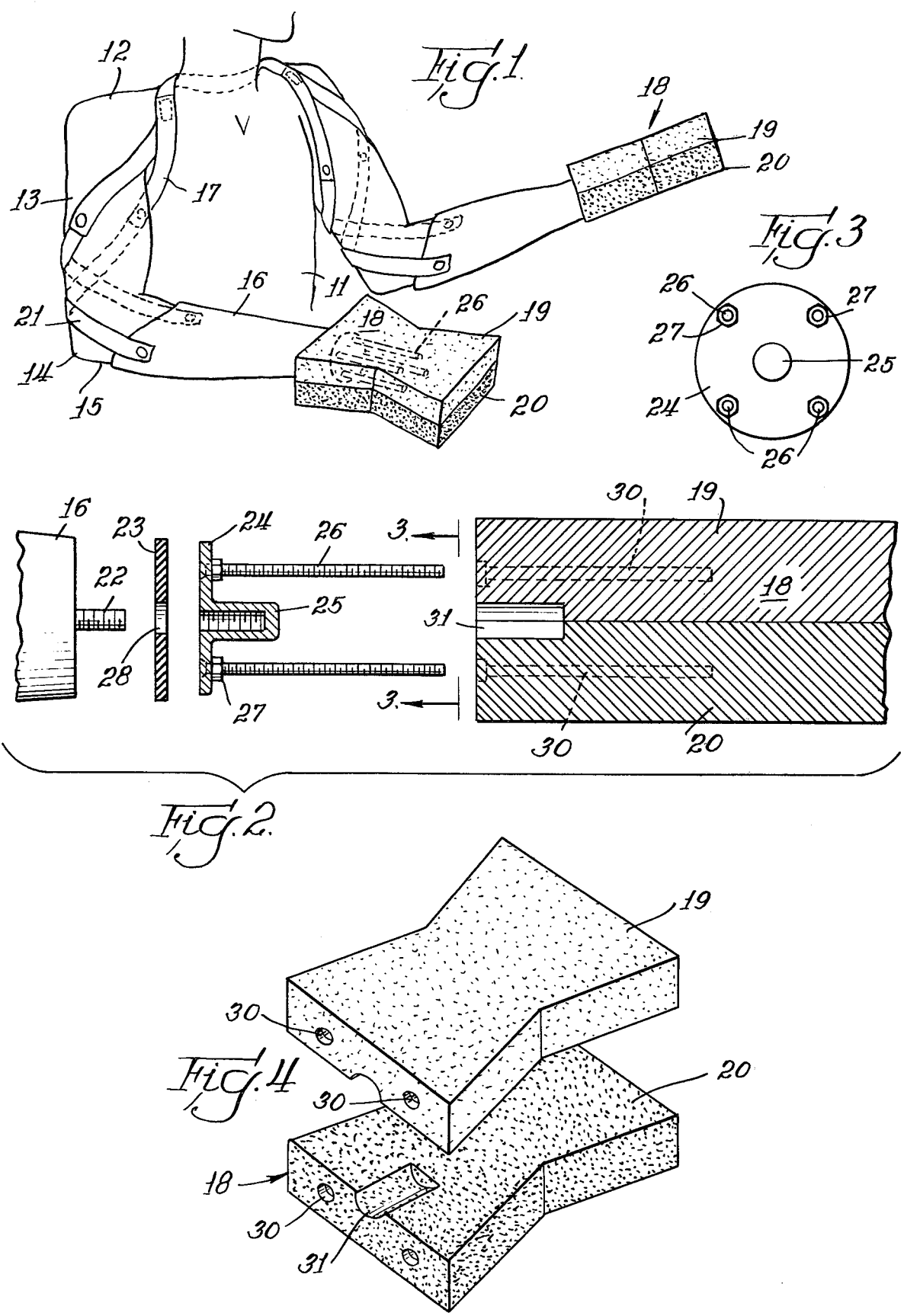

WASHING ATTACHMENT FOR ARTIFICIAL ARMS

BACKGROUND OF THE INVENTION

Heretofore, it has been extremely difficult for persons who have had both arms partially amputated to be able to wash or bathe themselves. If such an attempt is made with the standard prosthesis, which generally includes mechanical grasping elements, which are generally made of metal and are manipulated by wires, such members and the wires became wet and covered with soap which is difficult to wash off and dry. In addition, even though the metal parts were formed of stainless steel or the like, they nevertheless, after long periods of use, tended to pit and corrode in spots, particularly at pivots or joints.

SUMMARY OF THE INVENTION

The invention relates to an attachment for artificial arms which enables the wearer to bathe or wash, which attachment takes the place of the standard artificial arm utilized by amputees.

BRIEF DESCRIPTION OF THE DRAWINGS

FIG. 1 is a partial perspective view of the torso of a person having both arms amputated below the elbow with the attachments made in accordance with my invention attached to such person;

FIG. 2 is an expanded sectional view of the attachment for washing the body of an amputee;

FIG. 3 is a sectional view taken on line 3—3 of FIG. 2; and

FIG. 4 is a perspective view of the sponges or the like shown in FIG. 2.

DESCRIPTION OF THE PREFERRED EMBODIMENT

Referring to the drawing, numeral 11 designates generally the torso of an individual including shoulders 12, upper arms 13, elbows 14 and portions of lower arms 15. The extremities of the arms have been removed by amputation. Attached to the portions of the lower arms 15 which remain are artificial arms or prostheses 16 which are secured to the shoulders and upper arms of the user by a standard harness 17 consisting of straps which are secured together in a wellknown manner. Straps 21 secure the artificial arms 16 to the amputated lower arms 15 in the usual manner.

The artificial arms 16 which may be formed of any suitable material are provided with washing elements 18 at their lower extremities, which washing elements may consist of a fine sponge 19 and a coarse sponge 20 which may be secured together by any suitable adhesive. The end of the artificial arm 16 has secured thereto a threaded stud 22. A washer plate 23 and a plate 24 having an internally threaded member 25 formed thereon are provided with the plate 24 having, for example, four bolts 26 extending through apertures in the plate 24 and being secured thereto by nuts 27. The washer plate 23 having an aperture 28 therein for insertion over the stud 22 is first assembled on the arm 16 and thereafter the threaded aperture 25 is screwed on to the stud 22, the nuts and bolts 26 and 27 having already been attached to the plate 24. This assembly provides a structure necessary for attaching the sponge assembly 18 to the artificial arms 16. Preferably, adhesive material which is very sticky is applied to the bolts 26 and the bolts are inserted into openings 30 in the sponges 19 and 20 and retained therein due to the adhesive qualities of the coating. Likewise, the projection 25 is inserted into an opening 31 formed in the sponges 19 and 20 and this may also be covered with adhesive material to assist in retaining the sponge assembly 18 in position.

The artificial arms 16 are intended to replace the standard artificial arms (not shown) having the usual attachments thereon for enabling the amputee to grasp and hold objects. When the amputee wishes to wash or bathe, the standard artificial arms are removed and the artificial arms 16 with the sponge assemblies 18 are placed on the live portion 15 of the amputee's arms and, thereafter, are utilized for washing the body.

From the foregoing, it is apparent that I have provided a novel and inexpensive attachment for prosthesis for arms which will enable a person having either one or both arms partially amputated to wash or bathe a person's entire body.

What is claimed is:

1. An attachment for an artificial arm, comprising means for attaching the artificial arm and the attachment to a portion of a person's live arm to enable the person to bathe or wash,
said artificial arm having an extension at an extremity thereof,
said attachment comprising a sponge-like water retaining member positioned at said one extremity of said artificial arm opposite to the attaching means to the live arm,
said attaching means including standard straps for attaching the artificial arm to the live arm and to the body of the person,
and means for permanently securing the washing element to said one extremity of the artificial arm.

2. An attachment as claimed in claim 1 wherein the washing member is provided with an aperture therein for receiving the extension and includes means for adhesively securing said extension in the opening.

* * * * *